United States Patent [19]
Spievack et al.

[11] Patent Number: 5,871,484
[45] Date of Patent: Feb. 16, 1999

[54] APPARATUS AND METHOD FOR ADMINISTERING A BIOLOGICALLY ACTIVE SUBSTANCE TO A BONE

[75] Inventors: Alan R. Spievack, Cambridge; Douglas A. Fogg, Merrimac; Christopher P. Messina, Cambridge, all of Mass.

[73] Assignee: General Orthopedics, Cambridge, Mass.

[21] Appl. No.: 556,230

[22] Filed: Nov. 9, 1995

[51] Int. Cl.⁶ ..................................................... A61B 17/56
[52] U.S. Cl. ................... 606/60; 606/73; 606/72; 606/65; 604/93; 604/890.1; 604/285
[58] Field of Search ................... 606/62, 63, 65, 606/67, 72, 73, 86; 604/93, 890.1, 892.1, 285

[56] References Cited

U.S. PATENT DOCUMENTS

| | | | |
|---|---|---|---|
| 3,762,414 | 10/1973 | Burnhill | 128/285 |
| 3,976,072 | 8/1976 | Walker | 128/260 |
| 4,312,347 | 1/1982 | Magoon et al. | 128/260 |
| 4,326,522 | 4/1982 | Guerrero et al. | 128/260 |
| 4,711,251 | 12/1987 | Stokes | 604/890.1 |
| 4,772,261 | 9/1988 | Von Hoff et al. | 604/51 |
| 4,846,844 | 7/1989 | De Leon et al. | 623/66 |
| 4,863,444 | 9/1989 | Blömer | 604/304 |
| 5,062,829 | 11/1991 | Pryor et al. | 604/57 |
| 5,122,114 | 6/1992 | Miller et al. | 604/49 |
| 5,152,753 | 10/1992 | Laguette et al. | 604/93 |
| 5,207,644 | 5/1993 | Strecker | 604/93 |
| 5,281,226 | 1/1994 | Davydov et al. | 606/62 |
| 5,324,518 | 6/1994 | Orth et al. | 604/93 |
| 5,332,398 | 7/1994 | Miller et al. | 604/175 |
| 5,433,718 | 7/1995 | Brinker | 606/62 |

FOREIGN PATENT DOCUMENTS

| | | |
|---|---|---|
| 0140538 | 5/1985 | European Pat. Off. . |
| 0476503 | 3/1992 | European Pat. Off. . |
| 2806609 | 7/1979 | Germany . |
| 3533369 | 3/1987 | Germany . |
| 9208261 | 9/1992 | Germany . |
| 91/11148 | 8/1991 | WIPO . |
| 94/04085 | 3/1994 | WIPO . |

*Primary Examiner*—Michael Buiz
*Assistant Examiner*—Daphna Shai
*Attorney, Agent, or Firm*—Hamilton, Brook, Smith & Reynolds, P.C.

[57] ABSTRACT

A bone fastener is adapted to deliver biologically active substances to a bone site. An applicator is saturated with the substance and is disposed within an inner cavity of the fastener, near the bone site. Channels through the body of the fastener permit the substance to flow to the bone site. The substance can include therapeutic drugs, such as antibiotics, analgesics, bone morphogenic proteins, DNA, chemotherapy drugs and angiogenesis factors.

29 Claims, 6 Drawing Sheets

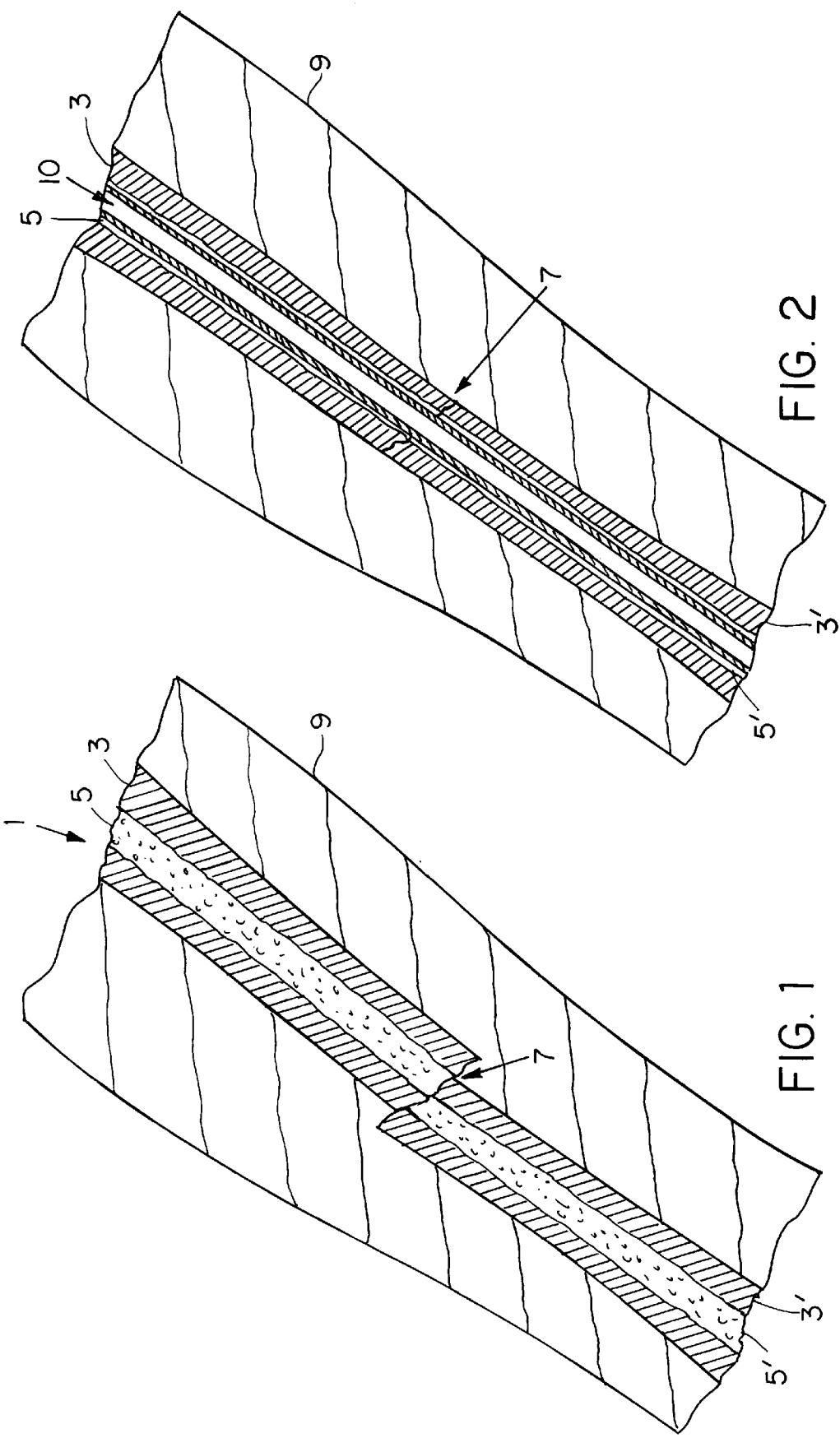

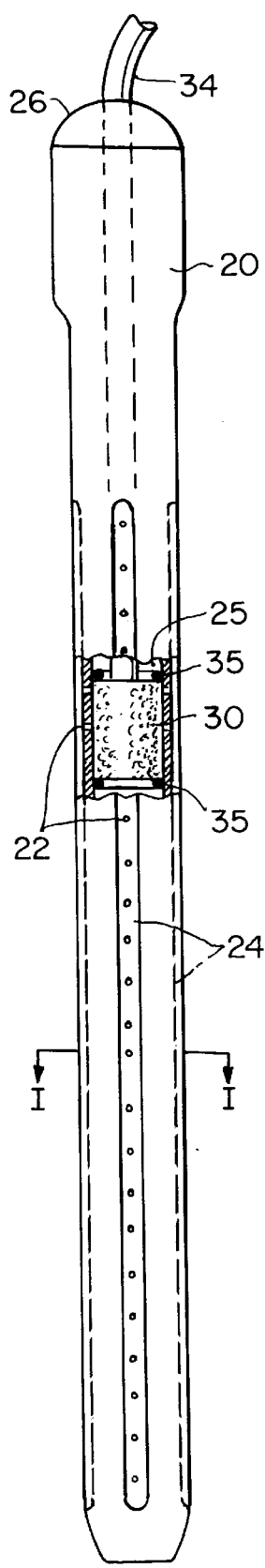
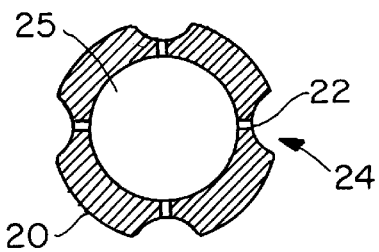
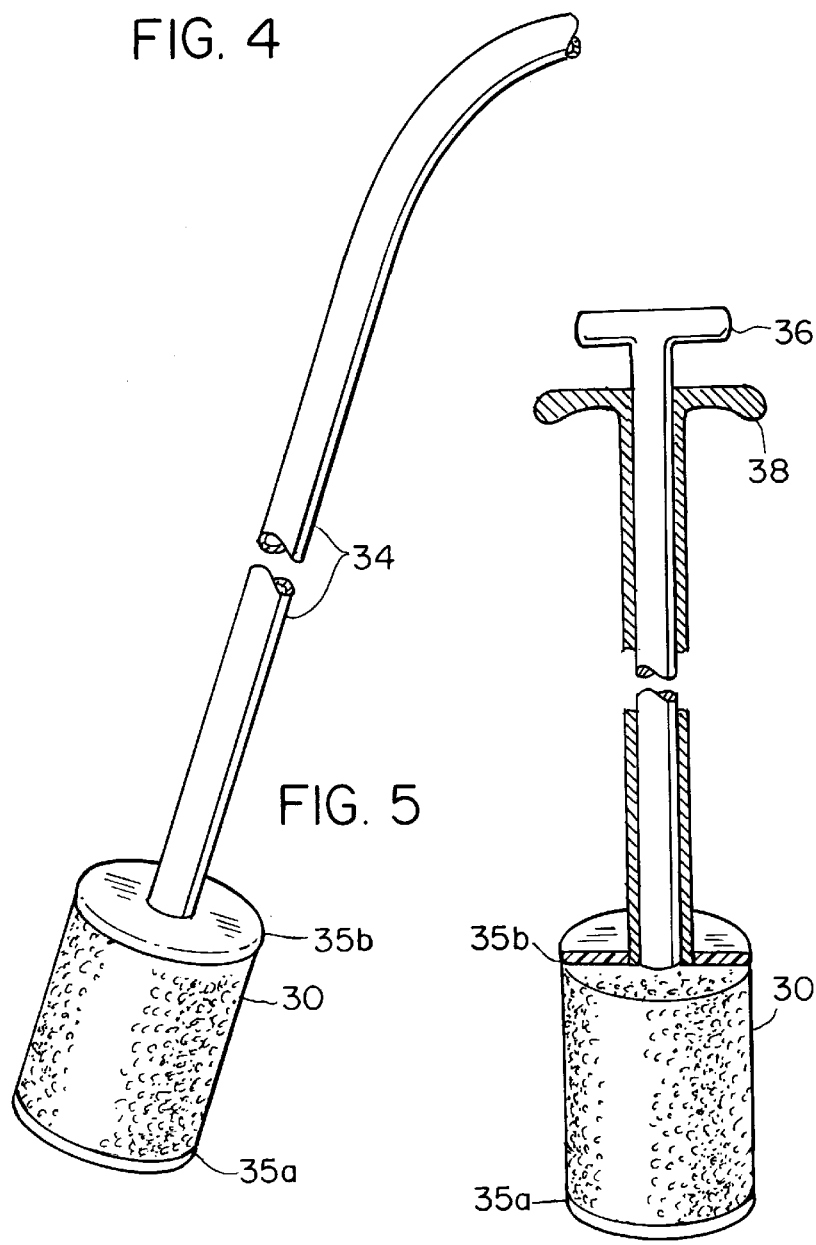
FIG. 3
FIG. 4
FIG. 5
FIG. 6

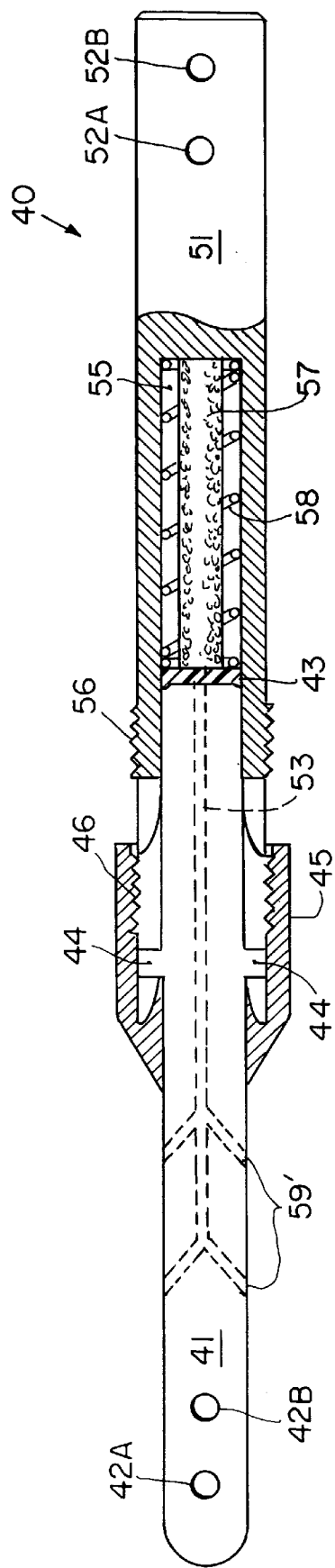
FIG. 7C
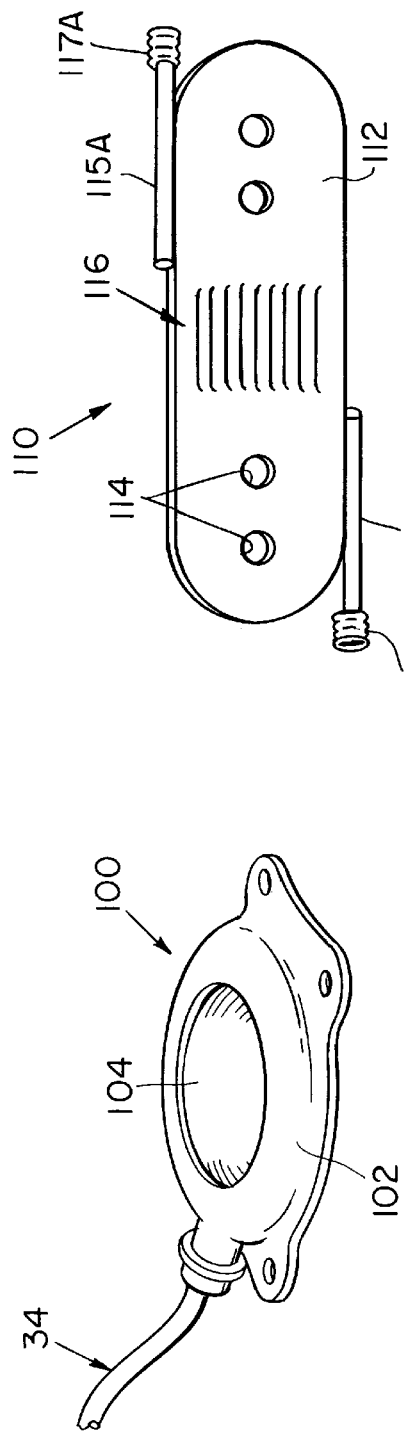
FIG. 14
FIG. 13

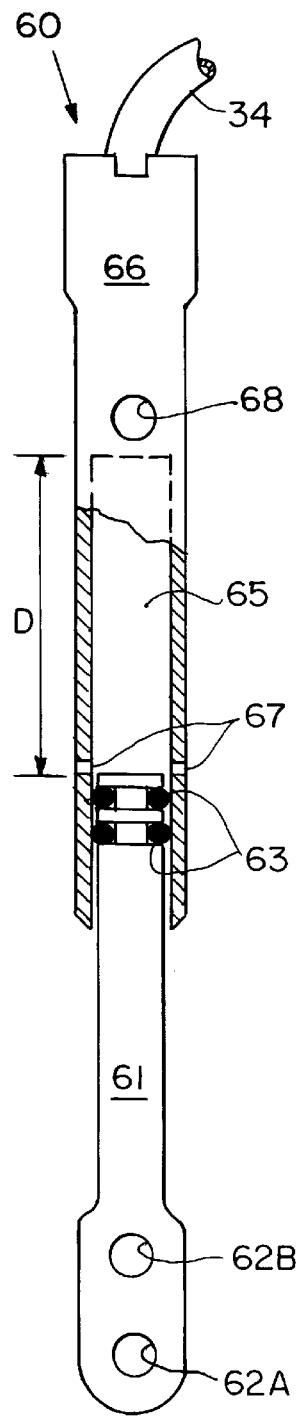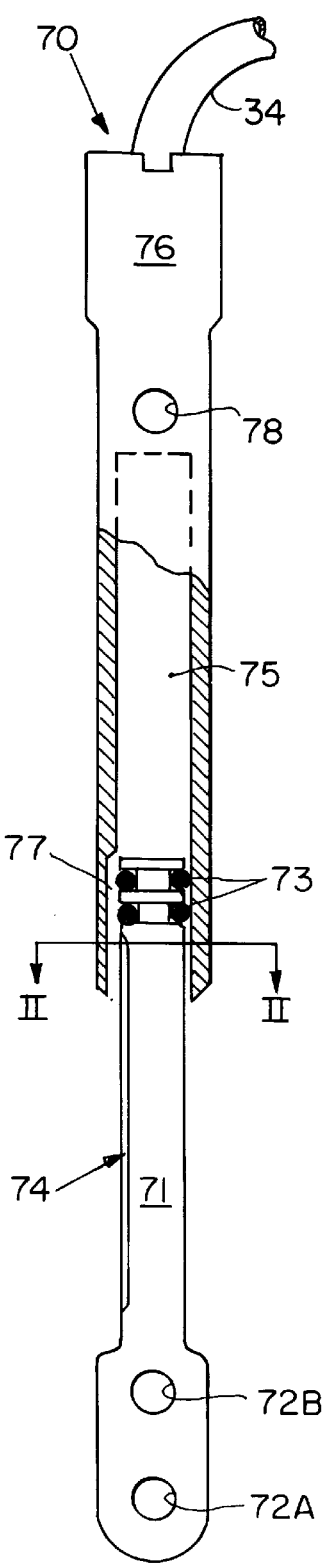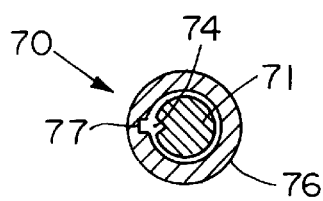
FIG. 8
FIG. 9
FIG. 10

APPARATUS AND METHOD FOR ADMINISTERING A BIOLOGICALLY ACTIVE SUBSTANCE TO A BONE

BACKGROUND OF THE INVENTION

Orthopedic fasteners have been used to repair bone fractures in the body of a human or other animal. For example, intramedullary nails are used to repair fractures in long bones of the body, such as the human femur. Intramedullary nails have also been used as a tool for lengthening femur bones, whereby the femur is surgically fractured and incrementally separated and allowed to regrow over time. In addition, reconstruction screws are used in hip reconstruction surgery and fracture plates are used for spine fractures.

In either case, an infection may occur at the fracture site or a bone growth factor may be required at the fracture site to stimulate bone growth. In those cases, further surgery may be required to deliver a therapeutic drug to the fracture site.

SUMMARY OF THE INVENTION

The invention solves or reduces the need for further invasive procedures by delivering biologically active substances, such as therapeutic drugs, to the fractured site of the bone through an implanted device. These therapeutic drugs include, but are not limited to, antibiotics, analgesics, bone morphogenic proteins, DNA, chemotherapy drugs and angiogenesis factors. Preferably, an intramedullary nail is used in a long bone of the body and is adapted to deliver the therapeutic drug. Besides fracture and osteotomy sites, the bone site can be a graft site. The invention, however, can be used to deliver therapeutic drugs to sites in other bones, such as hip bones or the spine, with a suitably adapted delivery structure, such as hip reconstruction screws or fracture plates. Similar devices can also be made in accordance with the invention to treat cartilage, such as in the knee.

In general, the invention relates to a device for administering a biologically active substance to a select bone site. The device includes a delivery structure which is implantable within, or attached to the surface of, a bone and is adapted to deliver the biologically active substance directly to the bone site. Preferably, the delivery structure is a bone fastener, such as an intramedullary nail, a reconstruction screw or a fracture plate.

A preferred embodiment of an intrabone fastener in accordance with the invention includes a fastener body which is adapted to be inserted into a selected bone. A cavity within the fastener body or a separate delivery structure stores the drug for delivery. There is at least one delivery channel extending from the cavity through the fastener body for delivering the therapeutic drug to the bone at a preselected bone site. Intrabone fasteners include intramedullary nails and reconstruction screws.

The cavity within the intrabone fastener can include an applicator or a collagen sponge saturated with the therapeutic drug. When the sponge is compressed by an external force, the drug is released from the sponge and flows through the delivery channels. In addition to a sponge or in conjunction therewith, a catheter can extend from the cavity of the fastener to the outside of the body or to an implanted reservoir accessibly via a needle so a physician can administer a dosage of the therapeutic drug to the bone site.

The foregoing and other objects, features and advantages of the invention, including various novel details of construction and combination of parts, will be apparent from the following more particular drawings and description of preferred embodiments of the apparatus and method for delivering a biologically active substance to a bone in which like reference characters refer to the same parts throughout the different views. The drawings are not necessarily to scale, emphasis instead being placed upon illustrating the principles of the invention. It will be understood that the particular bone fasteners embodying the invention are shown by way of illustration only and not as a limitation of the invention. The principles and features of this invention may be employed in varied and numerous embodiments without departing from the scope of the invention.

BRIEF DESCRIPTION OF THE DRAWINGS

FIG. 1 is a foreshortened cross-sectional schematic diagram of a limb having a fractured bone.

FIG. 2 is a partial cross-sectional diagram of the fractured bone of FIG. 1 with an intramedullary nail fixed in place.

FIG. 3 is a schematic diagram, partially in cross-section, of a preferred embodiment of the invention embodied in an intramedullary nail.

FIG. 4 is a cross-sectional schematic diagram taken along line I—I of FIG. 3.

FIG. 5 is a perspective view of an administering sponge system of FIG. 3.

FIG. 6 is a perspective view of another embodiment of an administering sponge system for use with the intramedullary nail of FIG. 3.

FIG. 7C is a schematic diagram, partially in cross section of another preferred embodiment of the invention embodied in a dynamized intramedullary nail.

FIG. 8 is a schematic diagram, partially in cross section, of a preferred embodiment of the invention embodied in a bone lengthening intramedullary nail.

FIG. 9 is a schematic diagram, partially in cross section, of another preferred embodiment of the invention embodied in a bone lengthening intramedullary nail.

FIG. 10 is a cross-sectional diagram taken along line II—II of FIG. 9.

FIG. 13 is a perspective view of an implantable reservoir for storing a biologically active substance in accordance with the invention.

FIG. 14 is a plan view of a preferred embodiment of the invention embodied in a fracture plate.

DETAILED DESCRIPTION OF PREFERRED EMBODIMENTS OF THE INVENTION

Figure 7A:
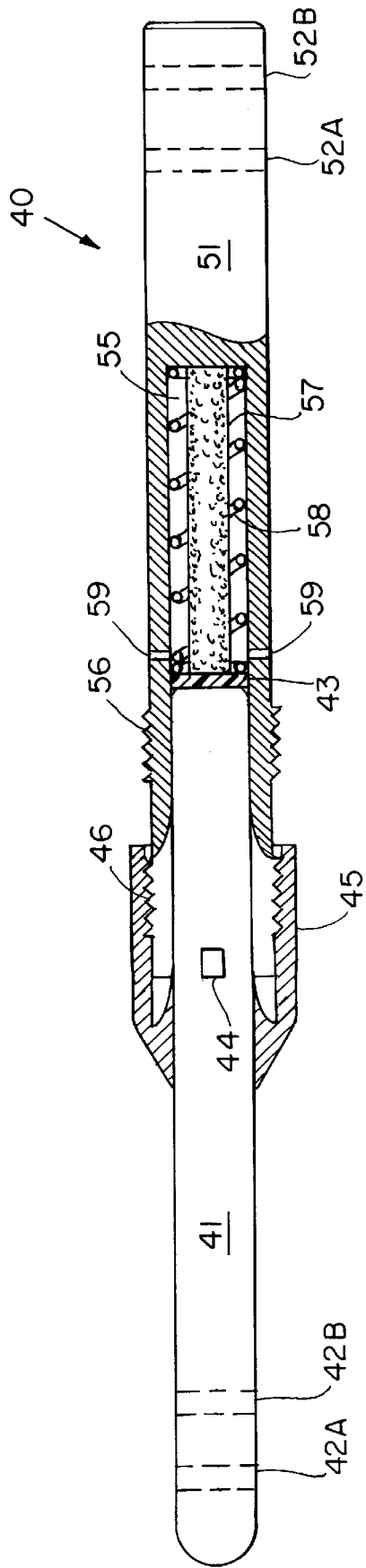
FIGS. 7A–7B are schematic diagrams, partially in cross section, of a preferred embodiment of the invention embodied in a dynamized intramedullary nail.

FIG. 1 is a foreshortened cross-sectional schematic diagram of a limb 9 having a fractured bone 1. Illustrated in the bone 1 are the bone cortex 3, 3' and the intramedullary canal 5, 5'. As illustrated, a fracture site 7 separates the bone 1 into two main sections: a proximal section nearer to the body and a distal section further from the body displaced from each other. The bone 1 can be repaired by reducing the fracture and fixing the two bone sections relative to each other with an orthopedic bone fastener.

FIG. 2 is a foreshortened cross-sectional schematic diagram of the fractured bone 1 of FIG. 1 having an intramedullary nail 10 fixed in place. The bone sections are first aligned (i.e., reduced) and the intramedullary nail 10 is inserted. Over time, the fracture site 7 is healed by bone cell growth. Once healed, the intramedullary nail 10 may be removed from the bone 1.

FIG. 3 is a schematic drawing, partially in cross-section, of a preferred embodiment of the invention embodied in an intramedullary nail. The nail has an elongate stainless steel body 20 with a hollow center cavity 25. As illustrated, a columned pattern of via openings 22 extend through the nail body 20 to elongate grooves 24 on the exterior of the nail body 20. The nail body 20, delivery channels or vias 22 and flow channels or grooves 24 can be more readily appreciated from FIG. 4.

FIG. 4 is a cross-sectional schematic diagram taken along line I—I of FIG. 3. The intramedullary nail is fluted by the grooves 24. Although the cross-section of the intramedullary nail is illustrated as being generally circular, other cross-sections can be employed in preferred embodiments of the invention. For example, the intramedullary nail can have a clover leaf cross-section and incorporate three columns of vias and grooves instead of the four columns shown.

Returning to FIG. 3, a storage member in the form of an applicator such as a sponge 30 is illustrated in the internal cavity 25 of the nail body 20. The sponge 30 is saturated with a biologically active substance which is later released into the bone through the vias 22 and down the grooves 24. Preferably, the sponge 30 is placed at or near the selected bone site. Seals 35 are disposed at the top and bottom of the sponge 30 to contain the biologically active substance in the cavity 25. A plurality of sponges can be placed in the intramedullary nail for treating numerous bone sites. Preferably the cross-section of the sponge 30 is adapted to match the cross-section of the cavity 25.

The physician measures the distance along the nail to the fracture site using x-ray images or a fluoroscope and positions the sponge 30 near a bone site; absolute precision in positioning the sponge 30 is not required. As illustrated, a catheter 34 extends from the sponge 30 through the top of the nail to the outside of the body. A physician can administer additional biologically active substances to the sponge 30 through the catheter 34. The top of the nail body 20 is sealed by a cannulated cap 26.

FIG. 5 is a perspective view of the applicator system of FIG. 3. The applicator system preferably includes a sponge 30 fabricated from collagen, for example. Illustrated is a bottom seal 35a, a top seal 35b, and the catheter 34. Preferably, the catheter 34 is sufficiently rigid so that the physician can move the sponge 30 longitudinally within the intramedullary nail to position the sponge 30 near to the bone site 38 based on the known distance along the nail.

FIG. 6 is a perspective view of another embodiment of an administering sponge system for use in the intramedullary nail of FIG. 3. A positioning handle 36 is connected to the bottom seal 35a and an activation handle 38 is connected to the top seal 35b. The positioning handle 36 is used by a physician to position the sponge near a selected bone site. Preferably, the sponge is saturated with the desired biologically active substance and the physician uses the activation handle 36 to squeeze the biologically active substance from the sponge. The activation handle 38 can operate as a pump to compress the sponge 30 between the seals 35a, 35b and lock into place or can activate a plunger which wrings out the sponge 30. In response, the biologically active substance flows out of the vias 22 and down the grooves 24 in the nail body 20 to treat the bone site. After use, the sponge 30 can be removed from the intramedullary nail.

Figure 7B:
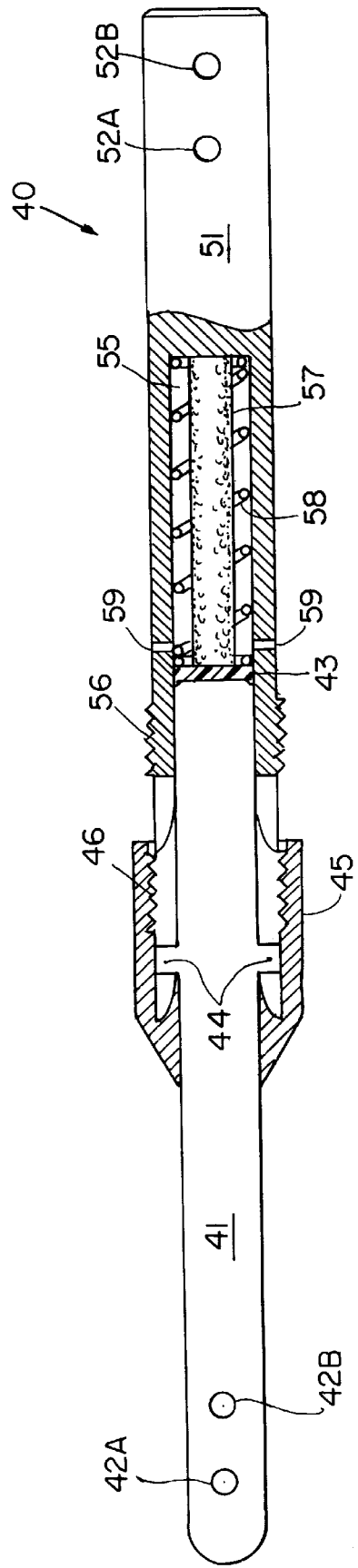

FIGS. 7A–7B are schematic diagrams, partially in cross-section, of the invention embodied in a dynamized intramedullary nail 40. The dynamized nail 40 includes a distal piston member 41 and a proximal cylinder member 51. The piston member 41 includes two fixation holes 42A, 42B and the cylinder member 51 includes two fixation holes 52A, 52B. The piston member 41 is fabricated so that it can be received in a chamber or cavity 55 of the cylinder member 51.

The piston member 41 and the cylinder member 51 are aligned by tabs 44 on the piston member 41. The tabs 44 align with slots 53 on the cylinder member 51. The assembly is locked together by a collar 45 having threads 46 which mate with threads 56 on the cylinder member 51. When so aligned and secured by the collar 45, the piston member 41 can move relative to the cylinder member 51 a distance determined by the length of the slots 53.

To resist compression of the piston 41 into the cylinder member 51, a spring member 58 is positioned within the cavity 55. The spring member 58 resist compressive forces exerted by the piston 41 and returns the piston to the extended position after being compressed. Preferably, the piston stroke is about 0.25 mm because longitudinal motion of the bone with an amplitude of about 0.25 mm is known to stimulate bone growth. Although the spring member 58 is illustrated as a coiled spring, the spring member 58 can be an elastomer, flat spring or belville washer.

In a preferred embodiment of the invention, an applicator such as a sponge 57 is also disposed within the cavity 55. The sponge 57 is saturated with a biologically active substance which, due to the compression of the spring member 58, is forced out of vias 59 through the body of the cylinder member 51. A seal 43 at the top of the piston member 41 creates an air seal around the cavity 55 and prevents the biologically active substance from seeping out through the joint between the piston member 41 and the cylinder member 51.

FIG. 7C is a schematic diagram, partially in cross section, of another preferred embodiment of the invention embodied in a dynamized intramedullary nail 40'. Unlike the intramedullary nail 40 of FIGS. 7A–7B, vias 59' are formed in the piston member 41 instead of the cylinder member 51. The vias 59' are connected to the inner cavity 55 by a central cannulation 53. Thus, when the spring member 58 is compressed, the biologically active substance is forced down the central cannulation 53 to the vias 59'. In all other respects, the intramedullary nail 40' of FIG. 7C is identical to the intramedullary nail 40 of FIGS. 7A–7B.

FIG. 8 is a schematic diagram, partially in cross-section, of a preferred embodiment of the invention embodied in a bone lengthening intramedullary nail 60. Illustrated is a proximal cylinder member 66 having a fixation hole 68 and vias 67. Vias 67 extend from the inner cavity 65 to the outer surface of the cylinder member 66. Also illustrated is a distal piston member 61 which includes fixation holes 62A, 62B and seals 63. In operation, the piston member 61 is extended outwardly from the cylinder member 66 by periodic finite amount until the bone is lengthened by a predetermined distance. Further details involving bone lengthening and suitable bone lengthening intramedullary nails are described by Alan Spievack in U.S. Pat. No. 5,350,379, the teachings of which are incorporated herein by reference.

Once the bone is extended to be the predetermined length, bone growth factors can be added to the osteotomy site to promote bone growth and hardening of the bone at the osteotomy site. In addition, once bone lengthening has stopped an antibiotic may need to be added to the bone site to fight infections. As illustrated, the bone lengthening nail 60 has a maximum extension distance D defined by the top of the cavity 65 and the via openings 67. The piston 61 is extended under hydraulic pressure through a catheter 34. Traditionally, saline is used as the hydraulic fluid. Once the piston member 61 has extended the distance D, the saline flows out of the vias 67. At that point, the biologically active substance can be added through the catheter 34. The biologically active substance will also flow out the vias 67 to treat the nearby bone site.

FIG. 9 is a schematic diagram, partially in cross-section, of another preferred embodiment of the invention embodied in a bone lengthening intramedullary nail 70. Like the intramedullary nail 60 of FIG. 8, this bone lengthening nail 70 includes a piston member 71 having fixation holes 72A, 72B and a cylinder member 76 having a fixation hole 78. A cavity 75 is formed within the cylinder member 76 and the piston member 71 moves longitudinally within the cavity 75. Fluid is introduced by the catheter 34 and seals 73 on the piston member 71 prevent the fluid from escaping from the cavity 75, thereby maintaining hydraulic pressure.

The intramedullary nail 70 includes a longitudinal delivery channel or slot 77 in the cylinder member 76 and a longitudinal flow channel or groove 74 in the piston member 71. When the bone is fully lengthened and the piston member 71 is fully extended within the cylinder member 76, fluid from the cavity 75 can flow out the slot 77 and down the groove 74. In this way, the biologically active substance can be therapeutically applied to a bone site which interfaces with the groove 74 in the piston member 71.

FIG. 10 is a cross-sectional diagram of the bone lengthening intramedullary nail 70 taken along line II—II of FIG. 9. Illustrated is the piston member 71 within the cylinder member 76. The groove 74 and the slot 77 are in alignment.

Figure 11:
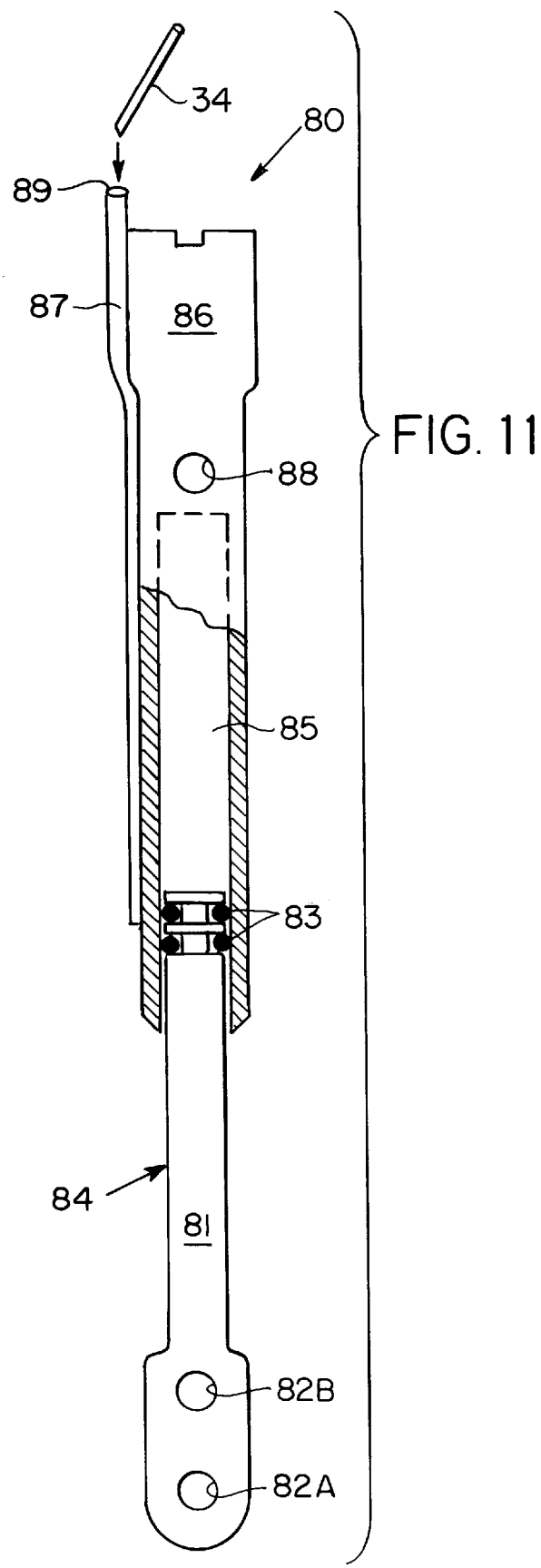
FIG. 11 is a schematic diagram, partially in cross section, of yet another preferred embodiment of the invention embodied in a bone lengthening intramedullary nail.

FIG. 11 is a schematic diagram, partially in cross section, of yet another preferred embodiment of the invention embodied in a bone lengthening intramedullary nail 80. Like the intramedullary nails 60, 70 of FIGS. 8 and 9, this bone lengthening nail 80 includes a piston member 81 having fixation holes 82A, 82B and a cylinder member 86 having a fixation hole 88. A cavity 85 is formed within the cylinder member 86 and the piston member 81 moves longitudinally within the cavity 85. Seals 83 on the piston member 81 prevent fluid from escaping from the cavity 85, thereby maintaining hydraulic pressure.

The intramedullary nail 80 includes a conduit 87 attached to the outside of the cylinder member 86. A catheter 34 supplying a biologically active substance connects to the conduit 87 at a connector 89. The biologically active substance from the catheter 34 flows down the conduit 87 to exit at a bone site.

The teachings of the invention can be applied to devices other than intramedullary nails. In particular, reconstruction screws for use in hip surgery can be modified according to the invention to deliver biologically active substances to a bone site within the hip.

Figure 12:
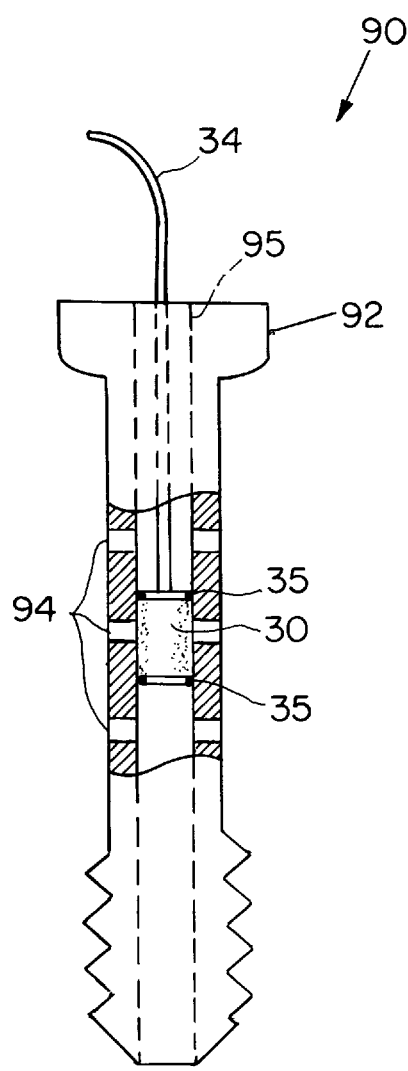
FIG. 12 is a cross-sectional schematic diagram of the invention embodied in an orthopedic screw.

FIG. 12 is a cross sectional schematic diagram of the invention embodied in an orthopedic screw 90. The orthopedic screw 90 includes a screw body 92 as cannulated to form an inner cavity 95. Vias 94 extend from the inner cavity 95 to the exterior of the screw body 92. An administrating system, such as a sponge 30, can be positioned relative to the vias 94 within the inner cavity 95. As described above, the sponge 30 is positioned using a distance measurement obtained by an x-ray or fluoroscope machine. Once positioned, a biological active substance can be applied to the sponge 30 through a catheter 34. The biologically active substance can then seep or be forced out through the vias 94 to a selected bone site. The sponge 30 can include top and bottom seals 35 to limit the dispersal of the biologically active substance to a particular region of the inner cavity 95.

The above embodiments of the invention can use a catheter 34 for transmitting the biologically active substance to the bone site. The biologically active substance can be introduced to the catheter through an exterior port on the body or from an implantable reservoir.

FIG. 13 is a perspective view of an implantable reservoir for storing a biologically active substance in accordance with the invention. The reservoir 100 includes a reservoir body 102 which defines an inner storage volume and a silastic access port 104. A physician can administer drugs to the reservoir 100 via a syringe and needle, with the needle penetrating the access port 104. By applying pressure to the access port 104, fluid from the reservoir 100 can also be forced through the catheter 34 under pressure. Such implantable reservoirs 100 can be obtained commercially from, for example, C. R. Bard.

Although the invention is well-suited to intrabone fasteners such as intramedullary nails and orthopedic screws, devices embodying the invention need not be positioned within a bone.

FIG. 14 is a plan view of a preferred embodiment of the invention embodied in a fracture plate. The fracture plate 110 includes a plate body 112 having fixation holes 114 therethrough. The fracture plate 110 is preferably used with fractures of the spine, wherein the fracture plate 110 is secured to the spine by the fixation holes 114. The fracture plate 110 includes grooves 116 formed from a biologically absorbable material such as polyglycolic acid (PGA) laced with a biologically active substance. When the fracture plate 110 is positioned, the grooves 116 are placed in contact with a fracture site. Over time, the biologically absorbable material releases the biologically active substances at the bone site.

The fracture plate 110 can include optional conduits 115A, 115B for infusion of biologically active substances or drainage from the plate location. The conduits 115A, 115B are preferably fabricated from a metal, such as stainless steel, and bonded to the fracture plate 110 by welding or otherwise. Each conduit 115A, 115 includes a connector 117A, 117B for coupling to a plastic infusion or drainage catheter. Preferably, one conduit 115A is used for infusion and the other conduit 115B is used for drainage, but both conduits 115A, 115B can be used for either infusion or drainage.

The dynamization technique can also be used with the fracture plate 110 to promote release of the biologically active substance from the grooves 116 or from other areas of the fracture plate 110. For example, dynamization can be accomplished by enlarging one or more of the fixation holes 114 and encasing the fixation hole with the biologically active substance embedded in a delivery compound, such as PGA.

Equivalents

While this invention has been particularly shown and described with reference to preferred embodiment thereof, it will be understood by those skilled in the art that various changes in form and details may be made therein without departing from the spirit and scope of the invention as defined by the appended claims. For example, similar devices can also be made to treat cartilage in the knees or elsewhere.

These and all other equivalents are intended to be encompassed by the following claims.

The invention claimed is:

1. A device for administrating a biologically active therapeutic substance to a bone of a body having a treatment site requiring therapeutic treatment comprising:

a delivery structure implantable within a body;

a delivery mechanism having a dynamization mechanism and coupled to the delivery structure to deliver a therapeutic substance to a selected the treatment site of a bone in response to motion of the body; and a replacement mechanism coupling the delivery structure to the outside of the body to facilitate replacement of the substance within the body.

2. The device of claim 1 wherein the delivery structure is a bone fastener having at least one channel through which the substance flows from inside the fastener to outside the fastener.

3. The device of claim 2 wherein the fastener is positionable so as to place a channel proximate to the treatment site of the bone.

4. The device of claim 1 wherein the delivery structure includes an internal cavity for storing the substance and at least one channel from the internal cavity to the exterior of the delivery structure.

5. The device of claim 4 further comprising a storage member disposed within the internal cavity to facilitate delivery of the substance over time.

6. The device of claim 5 wherein the replacement mechanism comprises a handle for withdrawal of the storage member from the body.

7. The device of claim 1 wherein the replacement mechanism comprises an infusion catheter extending from the delivery structure for providing a substance to the delivery structure under the control of a physician.

8. The device of claim 1 further comprising a drainage catheter extending from the delivery structure for draining fluid from the body.

9. The device of claim 1 wherein the delivery structure is implanted within the bone.

10. The device of claim 1 wherein the delivery structure is implanted adjacent to the bone.

11. An intramedullary nail for a bone having a medullary canal and a treatment site distally located along the medullary canal which requires therapeutic treatment comprising:

a fastener body shaped to be insertable through the medullary canal of a selected long bone of a body and to be extendable from a proximal entry point of the bone to a distal treatment site, the fastener body having a proximal fixation hole at a proximal end of the fastener body and a distal fixation hole at a distal end of the fastener body for securing the fastener body to the bone;

a cavity within the fastener body for storing a biologically active therapeutic substance; and an administrating member within the cavity and between the proximal fixation hole and the distal fixation hole to facilitate delivery of the substance over time;

a replacement mechanism coupling the administrating member to the outside of the body to facilitate replacement of the substance within the body; and at least one delivery channel extending from the cavity through the fastener body for delivering the substance from the administering member to the treatment site of the selected bone.

12. The intramedullary nail of claim 11 wherein the fastener body includes at least one flow channel on the exterior of the fastener body, each flow channel interfacing with at least one delivery channel to deliver the substance longitudinally along the fastener body.

13. The intramedullary nail of claim 11 wherein the administrating member is a sponge.

14. The intramedullary nail of claim 11 wherein the replacement mechanism comprises a catheter extending from the cavity for providing a substance to the cavity under the control of a physician.

15. The intramedullary nail of claim 11 further comprising a dynamization mechanism within the cavity to dynamize the fastener to urge deliver of the substance in response to motion of the body.

16. The intrabone fastener of claim 11 wherein the replacement mechanism comprises a handle for withdrawal of the administrative member from the body.

17. A method of fabricating an intramedullary nail for a bone having a medullary canal and a treatment site distally located along the medullary canal which requires therapeutic treatment, comprising the steps of:

forming a fastener body shaped to be insertable through the medullary canal of a selected long bone of a body and to be extendable from a proximal entry point of the bone to a distal treatment site;

forming a proximal fixation hole at a proximal end of the fastener body and a distal fixation hole at a distal end of the fastener body for securing the fastener body to the bone;

forming a cavity within the fastener body for storing a biologically active therapeutic substance;

disposing an administrating member within the cavity and between the proximal fixation hole and the distal fixation hole to facilitate delivery of the substance over time;

coupling a replacement mechanism between the administrative member and the outside of the body to facilitate replacement of the substance within the body; and forming at least one delivery channel extending from the cavity through the fastener body for delivering the substance from the administrative number to the treatment site of the selected bone.

18. The method of claim 17 further comprising the steps of:

forming at least one flow channel on the exterior of the fastener body; and interfacing each flow channel with at least one delivery channel to deliver the substance longitudinally along the fastener body.

19. The method of claim 17 wherein the administrating member is a sponge.

20. The method of claim 17 further comprising the step of disposing a spring member within the cavity to dynamize the fastener to urge deliver of the substance in response to motion of the body.

21. The method of claim 17 wherein the step of coupling comprises attaching an infusion catheter to the administrative member.

22. The method of claim 17 wherein the step of coupling comprises attaching a handle to the administrative member.

23. A device for administering a biologically active substance to a selected treatment site requiring therapeutic treatment within a body comprising:

a storage member for storing a biologically active therapeutic substance and being insertable within the body to a position proximate to the selected treatment site;

a replacement mechanism coupling the storage member to the outside of the body to facilitate replacement of the substance within the body; and an extraction mechanism having a dynamization mechanism for extracting the biologically active substance from the storage member in response to motion of the body.

24. The device of claim 23 wherein the storage member is a sponge.

25. The device of claim 23 wherein the extraction mechanism is a compression device.

26. The device of claim 23 wherein the extraction mechanism is a wringing device.

27. The device of claim 23 wherein the replacement mechanism comprises an infusion catheter extending from the storage member for introduction of a biologically active substance to the storage member.

28. The device of claim 23 wherein the replacement mechanism comprises a handle for withdrawal of the storage member from the body.

29. The device of claim 23 wherein the treatment site is on a bone.

* * * * *